United States Patent [19]

Duffett

[11] Patent Number: Plant 5,325

[45] Date of Patent: Nov. 6, 1984

[54] CHRYSANTHEMUM PLANT NAMED METEOR

[75] Inventor: William E. Duffett, Salinas, Calif.

[73] Assignee: Yoder Brothers, Inc., Barberton, Ohio

[21] Appl. No.: 463,924

[22] Filed: Feb. 4, 1983

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Meteor having semi-incurved capitulum form; decorative capitulum type; yellow ray floret color; diameter across face of capitulum ranging from 100 to 130 mm. at maturity; uniform nine week photoperiodic flowering response to short days; tall plant height when grown as a pinched disbud pot mum; semi-spreading branching pattern; and dual value as both pinched and standard disbud pot mums.

3 Drawing Figures

1

The present invention comprises a new and distinct cultivar of *Chrysanthemum morifolium*, Ramat., named Meteor.

Meteor is a product of a planned breeding program which had the objective of creating new chrysanthemum cultivars for pinched, disbut pot mum programs having decorative capitulum type, yellow ray floret color, nine week flowering response, and having the ability to produce commercially acceptable quality in year round programs. Such traits in combination were not present or required improvement in previously available commercial cultivars.

Meteor was originated from a cross made in a controlled breeding program in Salinas, Calif. in 1977. The female parent was Dark Yellow Paragon, disclosed in U.S. Plant Pat. No. 3,916, a spontaneous mutation from Yellow Paragon, disclosed in U.S. Plant Pat. No. 3,405, which in turn mutated from Paragon, disclosed in U.S. Plant Pat. No. 3,368, which was originated by the present inventor.

The male parent of Meteor was Wildfire, disclosed in U.S. Plant Pat. No. 3,236, which was originated from a cross between Mandalay (unpatented and commercially avilable) and an unnamed bronze decorative seedling.

Meteor was discovered and selected as one flowering plant within the progeny of the stated cross by William E. Duffett on Dec. 29, 1978 in a controlled environment in Salinas, Calif.

The first act of asexual reproduction of Meteor was accomplished when vegetative cuttings were taken from the initial selection in May 1979 in a controlled environment in Salinas, Calif. by a technician working under formulations established and supervised by William E. Duffett. Horticultural examination of selected units initiated July 1980 has demonstrated that the combination of characteristics as herein disclosed for Meteor are firmly fixed and are retained through successive generations of asexual reproduction.

Meteor has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

2

The following traits have been repeatedly observed and are determined to be basic characteristics of Meteor, which in combination distinguish this chrysanthemum as a new and distinct cultivar:

(1) Semi-incurved capitulum form;

(2) Decorative capitulum type;

(3) Yellow ray floret color;

(4) Diameter across face of capitulum ranging from 100 to 130 mm. at maturity;

(5) Uniform nine week photoperiodic flowering response to short days;

(6) Tall plant height, requiring 1–2 long day weeks prior to pinch and short days, and 1–2 applications of 2500 ppm B-9 after the beginning of short days to attain a flowered plant height of 30 to 40 cm.;

(7) Semi-spreading branching pattern; and (8) Dual value as both pinched and standard disbud pot mums.

The accompanying photographic drawings depict typical foliage and inflorescence characteristics of Meteor. Sheet 1 is a color photograph of a plant of Meteor grown as a pinched, disbud pot mum, with colors being as accurate as possible with renditions of this type. Sheet 2 is a black and white photograph of three views of the inflorescence of Meteor. Sheet 3 shows the leaves of Meteor in three stages of development (mature, intermediate, immature).

Of the many commercial cultivars known to the present inventor, the most similar in comparison to Meteor are Mountain Peak, disclosed in U.S. Plant Pat. No. 3,458, and Golden Bowl, disclosed in U.S. Plant Pat. No. 4,765. Reference is made to attached Chart A which compares certain characteristics of Meteor to those same characteristics of Mountain Peak and Golden Bowl.

Meteor, when compared to Mountain Peak, has deeper yellow color, more incurved capitulum form, a more spreading branching pattern, and one week earlier flowering response.

Meteor, when compared to Golden Bowl, has lighter yellow color, less incurved capitulum form, a less spreading branching pattern, and one week earlier flowering response.

In the following description, color references are made to The Royal Horticultural Society Colour Chart. The color values were determined between 10:00 A.M.

and 10:30 A.M. on Nov. 20, 1982 under 150 foot-candle light intensity at Salinas, Calif.

CLASSIFICATION

Botanical: *Chrysanthemum morifolium*, Ramat., cv Meteor.

Commercial: Disbud and standard decorative pot mum.

INFLORESCENCE

Capitulum:

*Form.*—Semi-incurved.

*Type.*—Decorative.

*Diameter across face.*—100 To 130 mm.

Corolla of ray florets:

*Color (general tonality from a distance of three meters).*—Yellow.

*Color (abaxial).*—7A-C Immature to 6A-C mature.

*Color (adaxial).*—9A-C Immature to 10A-B mature.

*Shape.*—Oblong with rounded tip.

Corolla of disc florets:

*Color (mature).*—3A-C.

*Color (immature).*—154B-C.

Reproductive organs:

*Androecium.*—Present disc florets only; scant pollen.

*Gynoecium.*—Present both ray and disc florets.

PLANT

General appearance:

*Height.*—Tall; 30 to 40 cm. given 2 long day weeks before pinch and lights out, and 1-2 applications 2500 ppm B-9 after lights out.

*Branching pattern.*—Semi-spreading.

*Foliage:*

*Color (abaxial).*—147A,B.

*Color (adaxial).*—148A.

*Shape.*—Shallow lobing. Moderately serrated.

CHART A

COMPARISON OF METEOR AND MOUNTAIN PEAK AND GOLDEN BOWL

| CULTIVAR | RAY FLORET COLOR | CAPITULUM FORM AND TYPE | BRANCHING PATTERN |
|---|---|---|---|
| METEOR | YELLOW TINGE OF BRONZE | SEMI-INCURVED DECORATIVE | SEMI-SPREADING |
| MOUNTAIN PEAK #3,458 | LIGHT YELLOW | FLAT DECORATIVE | SEMI-UPRIGHT |
| GOLDEN BOWL #4,765 | GOLDEN YELLOW TINGED BRONZE | INCURVED DECORATIVE | SPREADING |

| CULTIVAR | DIAMETER ACROSS FACE OF CAPITULUM | PLANT HEIGHT | FLOWERING RESPONSE PERIOD |
|---|---|---|---|
| METEOR | 100 to 130 mm. | TALL 30 to 40 cm. | 9 WEEKS |
| MOUNTAIN PEAK #3,458 | 100 to 130 mm. | MEDIUM 30 to 35 cm. | 10 WEEKS |
| GOLDEN BOWL #4,765 | 125 to 150 mm. | SHORT 25 to 30 cm. | 10 WEEKS |

COMPARISONS MADE OF PLANTS GROWN AS PINCHED DISBUD POT MUMS IN SALINAS, CALFORNIA

I claim:

1. A new and distinct cultivar of *Chrysanthemum morifolium*, Ramat., plant known by the cultivar name Meteor, as described and illustrated, and particularly characterized as to uniqueness by the combined characteristics of semi-incurved capitulum form; decorative capitulum type; yellow ray floret color; diameter across face of capitulum ranging from 100 to 130 mm. at maturity; uniform nine week flowering response; tall plant height; semi-spreading branching pattern; and dual value as both pinched and standard disbud pot mums.

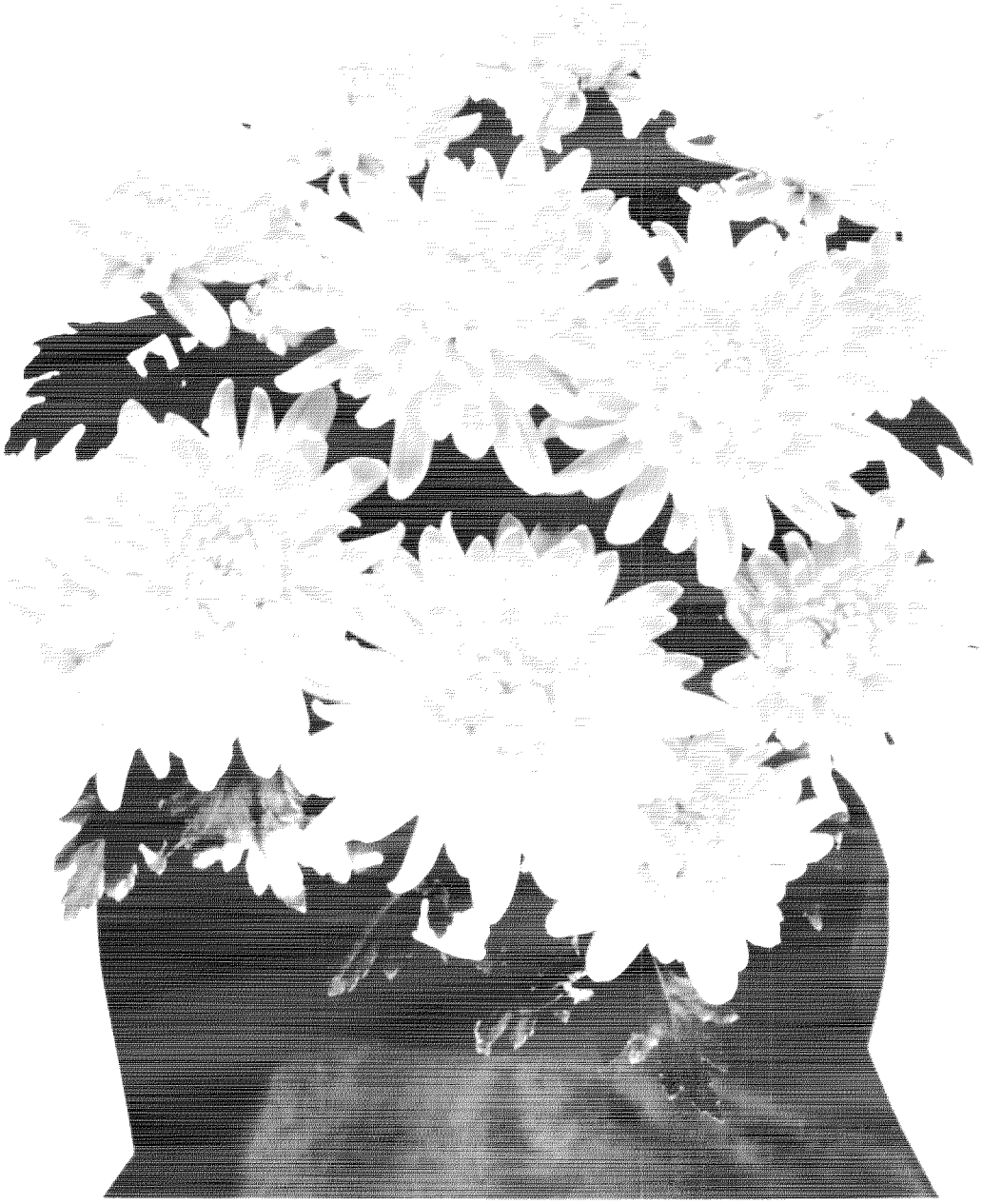

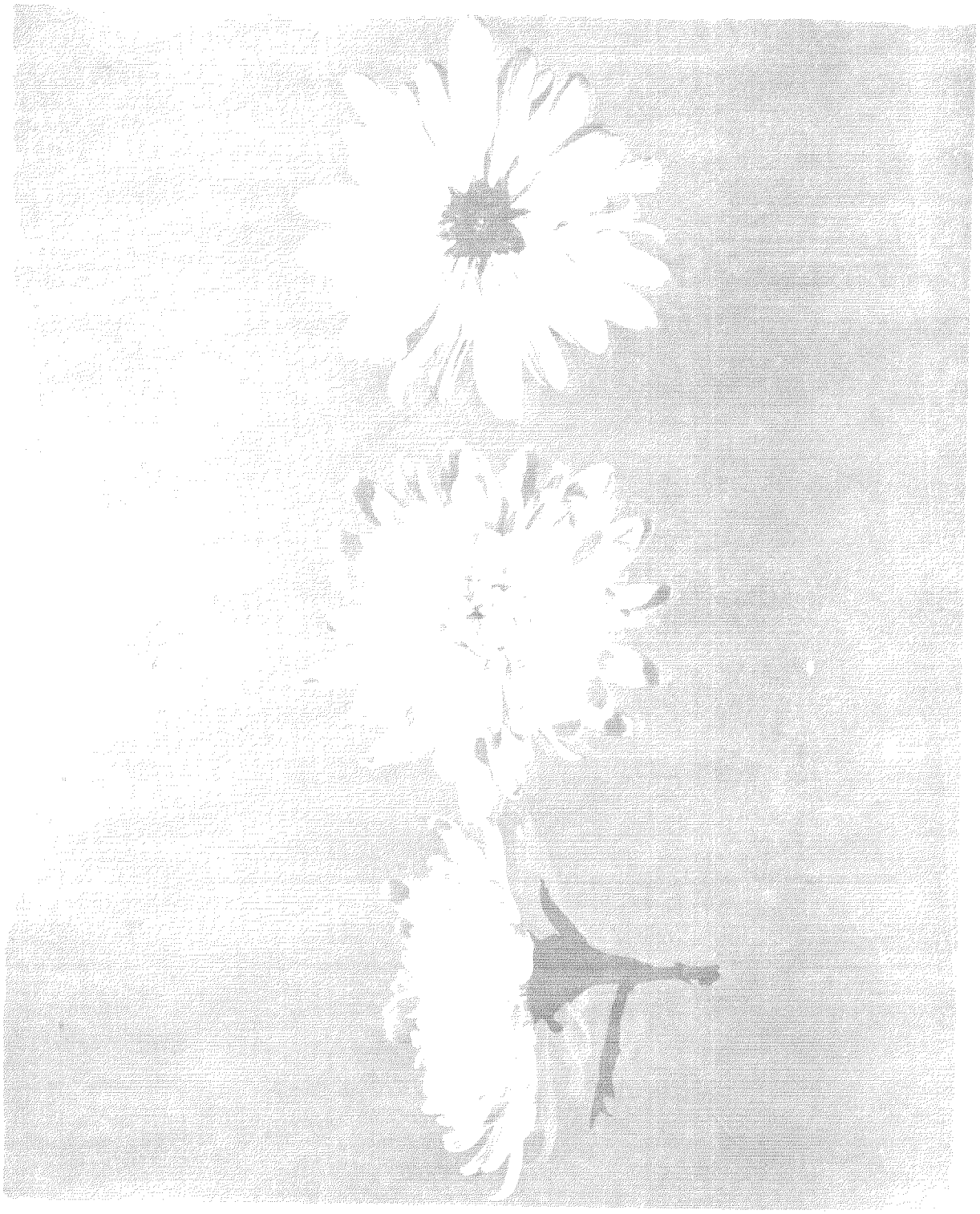

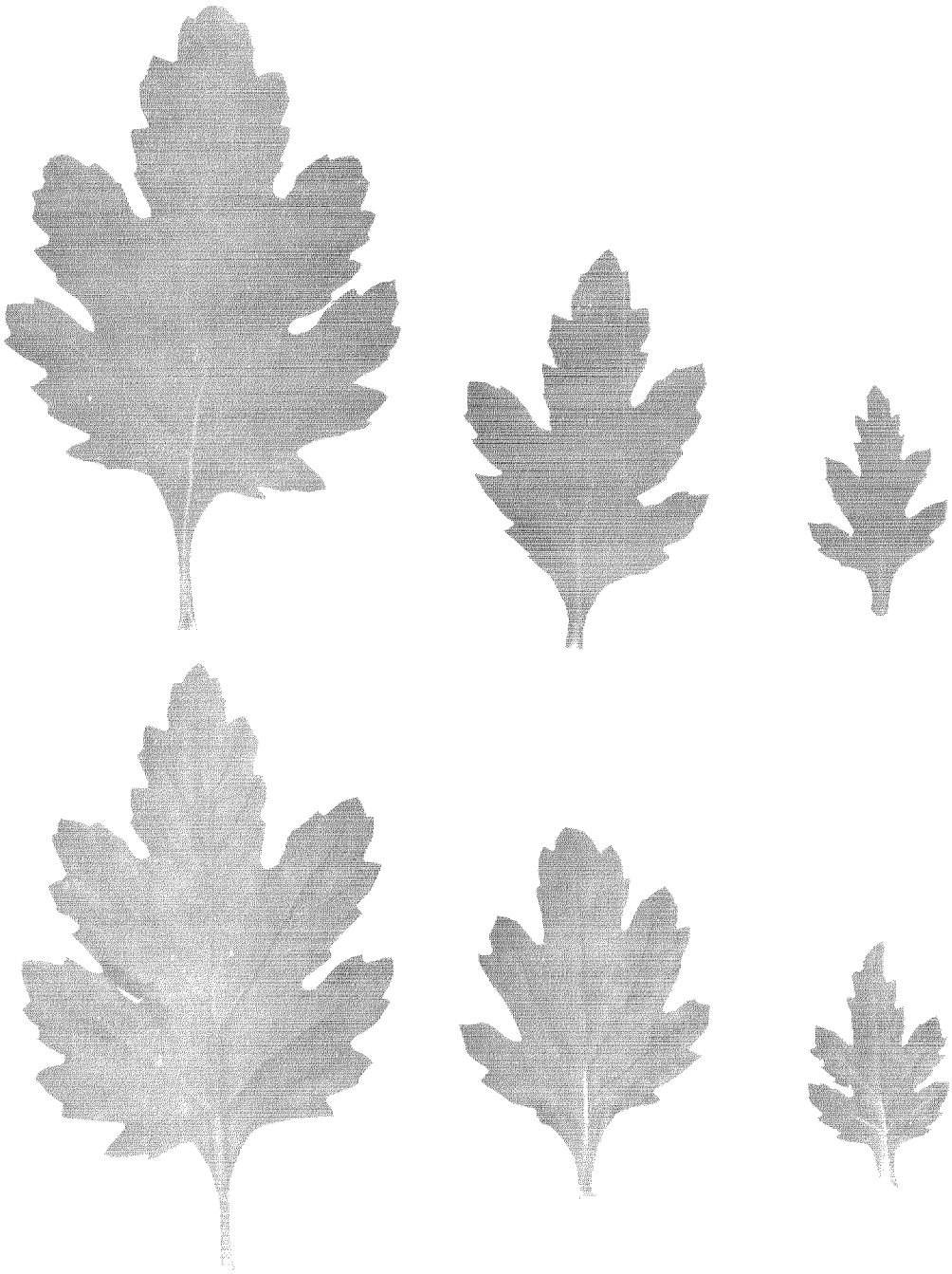

* * * * *